United States Patent [19]

Nickolson

[11] Patent Number: 5,055,449
[45] Date of Patent: Oct. 8, 1991

[54] VINCRISTINE-CONTAINING PRODUCT

[75] Inventor: Victor J. Nickolson, Oss, Netherlands

[73] Assignee: Akzo N.V., Arnhem, Netherlands

[21] Appl. No.: 268,117

[22] Filed: Nov. 7, 1988

[30] Foreign Application Priority Data

Oct. 11, 1987 [NL] Netherlands ................. 8702688

[51] Int. Cl.$^5$ ................. A61K 37/02; A61K 31/48
[52] U.S. Cl. ................................ 514/17; 514/16; 514/922; 540/478
[58] Field of Search ............... 514/16, 17, 922; 540/478

[56] References Cited

U.S. PATENT DOCUMENTS 3,842,064 10/1974 Greven ........................... 530/329
4,388,305 6/1983 Trouet et al. c ................. 514/17

OTHER PUBLICATIONS

Müller et al., "Neurons of the Snail *Lymnaea stapnalis* as a Model to Study the Neurotoxic Side Effects of Cytostatic Compounds . . . ".
Goodman et al., Pharmacological Basis of Therapeutics, 7th Ed., pp. 1277-1278.
Adwankar, J. K. et al., "Combination Chemotherapy of Early and Advanced Murine P388 Leukaemia with Bouvardin, cis-Diamminedichloroplatinum and Vincristine", Oncology, 41, 370-373 (1984).

Primary Examiner—Howard E. Schain
Assistant Examiner—Choon P. Koh
Attorney, Agent, or Firm—William M. Blackstone

[57] ABSTRACT

The present invention provides a pharmaceutical product for combating cancer with vincristine as active constituent, the neuropathic complications being prevented by a peptide. The product according to the invention contains:

(a) vincristine or a salt thereof, and
(b) a peptide having the general formula I:

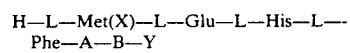

or a salt or an N-acyl derivative thereof in which Met(X) represents the amino acid radical Met, Met(O) or Met(O$_2$),
A represents the amino acid radical L-Lys, D-Lys, L-Arg or D-Arg,
B represents the amino acid radical L-Trp or L-Phe,
Y represents the hydroxyl group, an esterified hydroxyl group or an optionally substituted amino group.

7 Claims, No Drawings

VINCRISTINE-CONTAINING PRODUCT

The present invention relates to a vincristine-containing pharmaceutical product for treating various types of cancer.

Vincristine is a mitosis-retarding Vinca alkaloid which is fairly effective in combating various types of cancer, particularly Hodgkins disease and other types of blood cancer.

However, in the treatment of cancer patients with vincristine complications regularly occur after some time which are at first of a sensory nature and later also of a motor nature. These complications relate in general to a very heterogeneous group of neurological syndromes which often overlap each other. In a number of cases, the previously mentioned complications have proven to be irreversible so that it is naturally beneficial for the patient if the complications concerned do not occur at all.

Sensory complications often manifest themselves in the form of pain and motor complications in the form of muscle weakness.

These neuropathic side effects or complications of vincristine can be largely prevented or mitigated by administering vincristine according to a very careful dosing system which particular daily or weekly maximum doses must not be exceeded.

It is, however, readily apparent that these dosage ceilings seriously affect the therapeutic scope of vincristine. In other words, a clear need exists for a vincristine product which contains higher dosages of vincristine and can thus operate more effectively in combating cancer without the previously mentioned neuropathic complications occurring.

The present invention therefore provides a pharmaceutical product for combating cancer with vincristine as active constituent, the neuropathic complications mentioned being prevented.

The product according to the invention comprises:
(a) vincristine or a salt thereof, and
(b) a peptide having the general formula I:

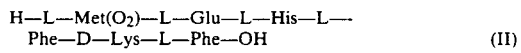

or a salt or an N-acyl derivative thereof in which Met(X) represents the amino acid radical Met, Met(O) or Met(O$_2$), A represents the amino acid radical L-Lys, D-Lys, L-Arg or D-Arg, B represents the amino acid radical L-Trp or L-Phe, Y represents the hydroxyl group, an esterified hydroxyl group or an optionally substituted amino group.

As a result of this combined treatment of a patient with vincristine and the peptide according to formula I, it becomes possible to administer vincristine in higher and/or more frequent dosages than hitherto has been the case, which has a highly beneficial effect on the therapeutic effectiveness of vincristine in the treatment of cancer.

In addition to vincristine itself, the pharmaceutically acceptable salts of vincristine, in particular the sulphate salt, are also included.

Peptides having the general formula I and salts thereof are known. For the preparation of such peptides reference is made, for the sake of brevity, to U.S. Pat. No. 3,842,064 and European Patent Application 179,332. These peptides are known in particular for their effect on memory and/or learning processes.

Within the scope of the present invention, use is preferably made of those peptides according to formula I in which Met(X) represents the amino acid Met(O$_2$) (methionine sulphone) and Y represents a hydroxyl group, a hydroxyl group which is esterified with an aliphatic alcohol containing 1 to 18 carbon atoms (and preferably a lower aliphatic alcohol containing 1 to 6 carbon atoms) or a substituted amino group of the type —NH—ALK—NH$_2$, in which ALK represents an alkylene group containing 2 to 10 carbon atoms, preferably 4 to 10, and more particularly, 7 or 8 carbon atoms.

A peptide having the formula II:

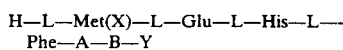Phe—D—Lys—L—Phe—OH    (II)

or a salt thereof is more particularly to be preferred within the scope of the present invention.

As used herein, N-acyl derivatives of the peptides having formula I means those peptides I which are acylated at the N-terminal end with a lower (1-8 C) aliphatic mono- or dicarboxylic acid such as acetic acid, propionic acid, butyric acid, malonic acid, succinic acid or glutaric acid.

The pharmaceutical product according to the invention is preferably used subcutaneously or intranasally and is furthermore preferably administered in the form of a liquid containing the two active substances simultaneously.

For subcutaneous administration in the form of an intramuscular, but particularly in the form of an intravenous injection product, the two active substances involved, vincristine and the peptide according to formula I, are dissolved, suspended or emulsified in a liquid suitable for injection. A solution of the two substances in water is, however, preferable in this connection.

For intravenous administration in the form of an infusion, the two substances are dissolved in a pharmaceutically acceptable solvent, preferably water, in a concentration suitable for infusion.

For intranasal administration, the two substances involved are introduced into a medium suitable for intranasal administration and administered by means of a propellent gas or spray mechanism.

The dosaging of the two substances in the product according to the invention depends to a large extent on the individual need of the patient. Vincristine is in general administered in a dosage of 1.5–5 mg per week, the preference being for injection once or twice a week.

The intravenous injection product according to the invention therefore contains preferably between 1.5 and 10 mg of vincristine in a concentration of 0.5–2 mg per milliliter.

The quantity of the peptide according to the general formula I is, of course, dependent on the quantity of vincristine chosen but said peptide is preferably present in said preparation in a quantity of $2 \times 10^{-4}$ to $2 \times 10^{-3}$ mmol per ml and, more particularly, between $4 \times 10^{-4}$ and $8 \times 10^{-4}$ mmol per ml.

An eminently suitable injection product according to the invention contains between 0.5 and 2 mg of vincristine per milliliter and between 0.35 and 0.65 mg per milliliter of the peptide according to formula II (molecular weight 870).

If the molecular weight of the peptide according to formula I to be used is higher or lower than that of the peptide mentioned above having formula II, then the preferred dosage given should be modified accordingly.

It is obvious that different quantities have to be used for infusion liquids. However, these quantities are in general chosen so that the weekly dosage of the two substances in question to be administered corresponds in broad outlines to the dosage described above (of the substances concerned) when administered by way of one or more injections.

In addition to the peptides mentioned above, the product according to the invention may contain still other substances, in particular:

antimicrobial substances such as methyl p-hydroxybenzoate or benzyl alcohol, substances intended to render the product according to the invention isotonic, and substances which are capable of adjusting the pH of an aqueous solution of the product according to the invention.

Although the combination preparation as described above is to be preferred, the obvious alternative of providing a medicament (e.g. a two compartment syringe) in which the two active compounds are stored separately and are eventually combined just before the actual administration to the patient, also belongs to one of the embodiments of the present invention.

In another embodiment of the present invention the two active substances are separately administered to the patient.

In relation to the pH, attention is further drawn to the fact that this is preferably adjusted to a pH between 5 and 6.5; a slightly basic pH may, however, also be used.

The product according to the invention is further illustrated by reference to the following example.

A solution is prepared which contains per milliliter:

| | |
|---|---|
| the peptide having formula II | 0.5 mg |
| vincristine sulphate | 1 mg |
| methyl p-hydroxybenzoate | 1 mg |
| sodium acetate trihydrate | 1.36 mg |
| sodium chloride | 7 mg |
| hydrochloride acid and sodium hydroxide | to pH 5.5 |
| water for injection | to 1 ml |

I claim:

1. Pharmaceutical product for treating a patient believed to be suffering from a cancer susceptible to treatment by vincristine with high doses of vincristine or a salt thereof while mitigating the neuropathic side effects associated with vincristine comprising:

(a) vincristine or a salt thereof, and
(b) a peptide having the general formula I:

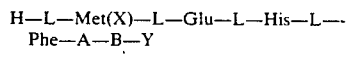
[I]

or a salt or N-acyl derivative thereof in which Met(X) represents the amino acid radical Met, Met(O) or Met(O$_2$), A represents the amino acid radical L-Lys, D-Lys, L-Arg or D-Arg, B represents the amino acid radical L-Trp or L-Phe, Y represents the group Gly-Z or Z, and Z represents the hydroxyl group, an esterified hydroxyl group or an optionally substituted amino group whereby greater quantities of vincristine can be administered in combination with said peptide than without said peptide.

2. Product according to claim 1, wherein the peptide according to formula I is: H—L—Met(O$_2$)—L—Glu—L—His—L—Phe—D—Lys—L—Phe—OH or a salt thereof.

3. Product according to claim 1 in a composition suitable for intravenous injection.

4. Product according to claim 1 in a composition suitable as an infusion product.

5. Intravenous injection product according to claim 3, comprising 0.5–2 mg of vincristine or a salt thereof per ml and $10^{-4}$ to $2 \times 10^{-3}$ mmol per ml of the peptide according to formula I or a salt of an N-acyl derivative thereof.

6. Product according to claim 5, comprising 0.5–1.5 mg of vincristine or a salt thereof per ml and 0.35–0.65 mg of the peptide having the formula H—L—Met(O$_2$)—L—Glu—L—His—L—Phe—D—Lys—L—Phe—OH (molecular weight 870) or a salt thereof.

7. A method of treating a patient believed to be suffering from a cancer susceptible to treatment by vincristine comprising administering to said patient an amount effective for retarding mitosis of (a) vincristine or a salt thereof, and
(b) a peptide of formula

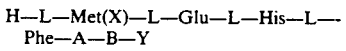
[I]

or a salt or N-acyl derivative thereof, wherein the amount of said peptide is sufficient to mitigate the neuropathic side effects associated with vincristine and the amount of vincristine administered is greater than that which could be administered without the peptide.

* * * * *